United States Patent
Gracey et al.

[11] Patent Number: 5,919,916
[45] Date of Patent: Jul. 6, 1999

[54] 6-O-ALKYL DERIVATIVES OF ERYTHRONOLIDE B

[75] Inventors: H. Eugene Gracey, Lindenhurst; Stephen H. Montgomery, Vernon Hills, both of Ill.; David A. Riley, Kenosha, Wis.; Jih-Hua Liu, Green Oaks, Ill.

[73] Assignee: Abbott Laboratories, Abbott Park, Ill.

[21] Appl. No.: 08/980,919

[22] Filed: Dec. 1, 1997

[51] Int. Cl.⁶ ..................................................... C07H 17/08
[52] U.S. Cl. ............................... 536/7.2; 536/7.4; 536/7.5
[58] Field of Search ................................ 536/7.2, 7.4, 7.5

[56] References Cited

U.S. PATENT DOCUMENTS

| | | |
|---|---|---|
| 4,331,803 | 5/1982 | Watanabe et al. . |
| 4,496,717 | 1/1985 | Adachi et al. . |
| 4,668,776 | 5/1987 | Yamada et al. . |
| 4,670,549 | 6/1987 | Morimoto et al. . |
| 4,672,109 | 6/1987 | Watanabe et al. . |
| 4,680,386 | 7/1987 | Morimoto et al. . |
| 5,141,926 | 8/1992 | Weber et al. . |
| 5,274,085 | 12/1993 | Amano et al. . |

FOREIGN PATENT DOCUMENTS

0260938 A2  3/1988  European Pat. Off. .

OTHER PUBLICATIONS

27th Annual Interscience Conference on Antimicrobial Agents and Chemotherapy J.B. McAlpine, et al., "Minor Products from the Microbial Transformation of 6–O–Methylerythromycin A by *Mucor Circinelloides*".

*Primary Examiner*—James O. Wilson
*Attorney, Agent, or Firm*—Portia Chen; Mona Anand

[57] ABSTRACT

Novel 6-O-alkyl derivatives of erythronolide B are provided. A process for the preparation of 6-O-alkyl derivatives of erythronolide B using erythromycin B is also provided. A process for preparing 6-O-alkyl derivatives of erythromycin C using novel 6-O-alkyl derivatives of erythronolide B is further provided.

13 Claims, No Drawings

6-O-ALKYL DERIVATIVES OF ERYTHRONOLIDE B

DESCRIPTION

1. Technical Field of the Invention

The present invention relates to erythromycin derivatives. More particularly, the present invention pertains to 6-O-alkyl derivatives of erythronolide B and processes for preparing 6-O-alkyl derivatives of erythronolide B.

2. Background of the Invention

Erythromycin derivatives A through D are known in the art and are clinically useful, broad-spectrum macrolide antibiotics. These compounds may be produced in a number of ways. One method of preparing erythromycins A through D is disclosed in U.S. Pat. No. 5,141,926. The proposed biosynthesis shown in FIG. 1 of that patent (also shown below) involves using 6-deoxyerythronolide B to produce erythromycin A.

As displayed in the diagram below, the first step is to make 6-deoxyerythronolide B by enzymatically assembling propionyl and 2-methyl malonyl thioesters (Process 1). Hydroxylation at the 6-carbon position of 6-deoxy erythromycin B with cytochrome P450 results in the formation of erythronolide B (Process 2). Two deoxysugar addition steps follow, with the first addition occurring at the 3-carbon position to produce 3-"-mycarosyl erythronolide B (Process 3). The second deoxysugar addition is at the 5-carbon position which results in the formation of erythromycin D (Process 4). At this point, two possible paths may be utilized to obtain erythromycin A. Under the first path, hydroxylation of erythromycin D at the 12-carbon position produces erythromycin B (Process 5). After hydroxylation, erythromycin B is O-methylated using O-methyl transferase at the 3"-position to produce erythromycin A (Process 6). The second path reverses the O-methylation and hydroxylation steps and produces erythromycin B (Process 6') before finally producing erythromycin A (Process 5').

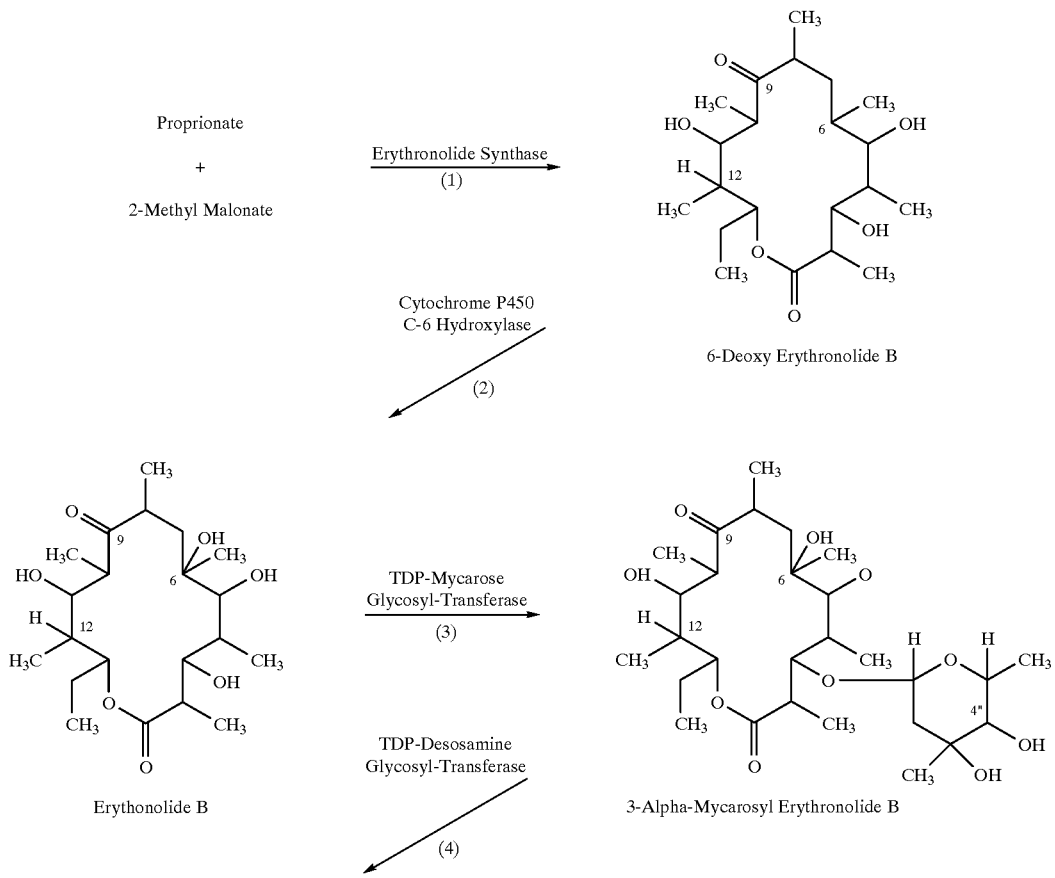

Proposed Metabolic Pathway for Biosynthesis of Erythromycin A
(U.S. Pat. No. 5,141,926)

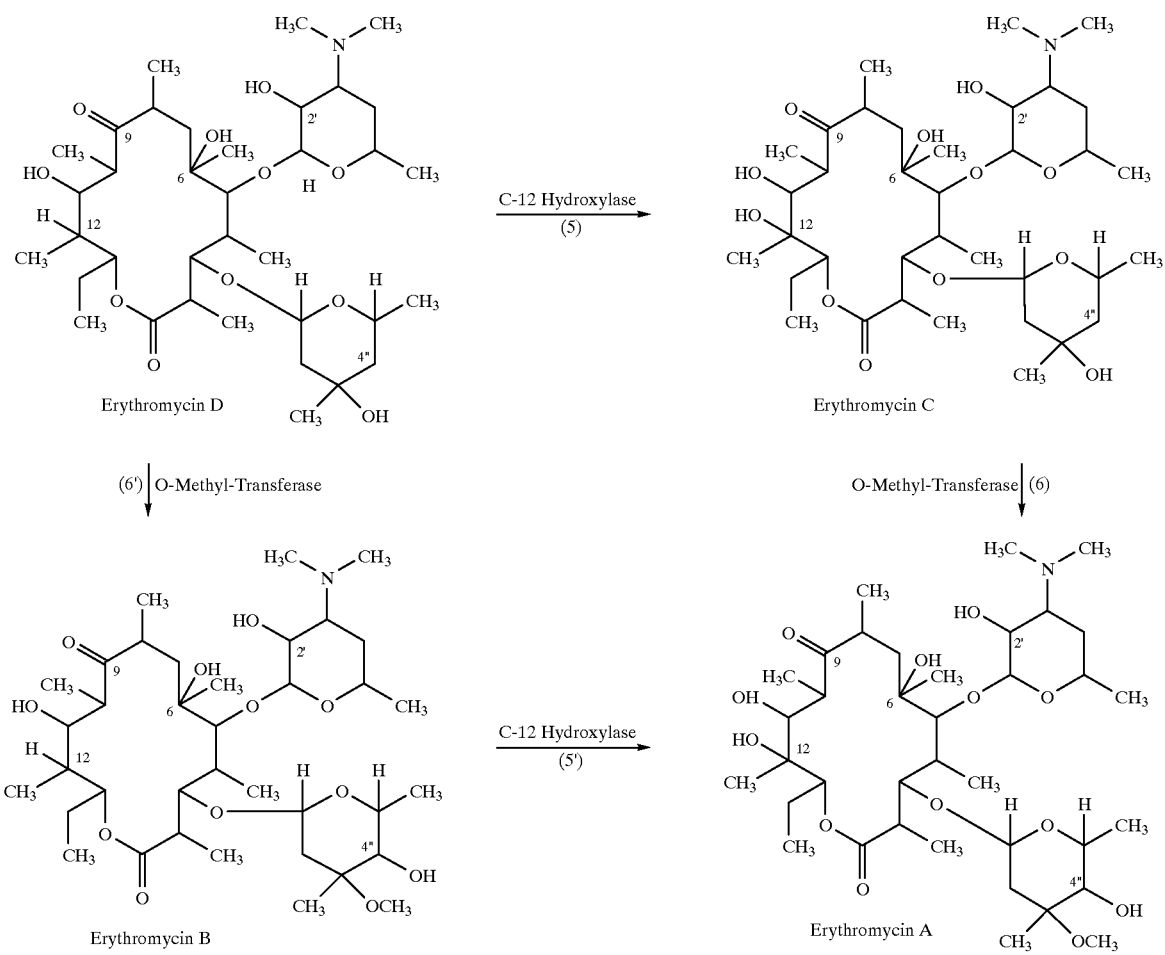

Generally, 6-O-alkyl derivatives of erythromycin are known as antibacterial agents. In particular, both 6-O-methyl erythromycin A (U.S. Pat. No. 4,331,803) and 6-O-methyl erythromycin B (U.S. Pat. No. 4,496,717) are potent macrolide antibiotics. The structures of both compounds are displayed below:

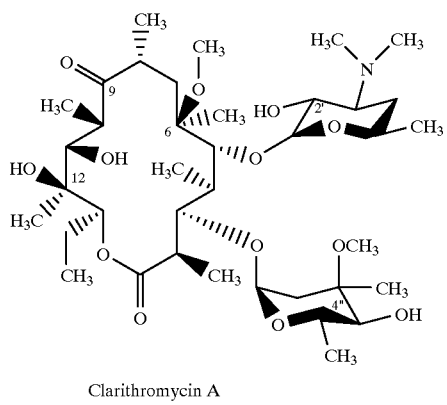

Clarithromycin A

-continued

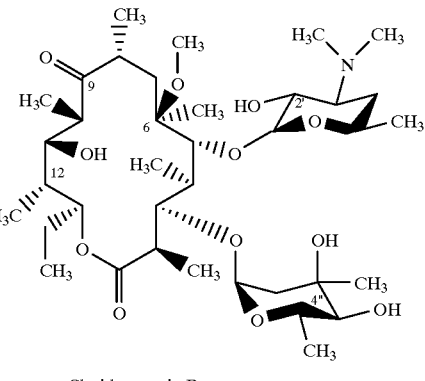

Clarithromycin B

It is possible to prepare 6-O-alkyl derivatives of erythromycin A only after producing erythromycin A from methods similar to the one described above. A variety of methods for preparing 6-O-methyl erythromycin A have been described. 6-O-methyl erythromycin A can be prepared by methylating a 2'-O-3'-N-dibenzyloxycarbonyl-des-N-methyl derivative of erythromycin A (U.S. Pat. No. 4,331,803). It can also be made from 9-oxime erythromycin A derivatives (See, e.g., U.S. Pat. Nos. 5,274,085; 4,680,386; 4,668,776; 4,670,549 and 4,672,109 and European Patent Application 0260938A2). In this process, the oxime is protected during methylation with a 2-alkenyl group (U.S. Pat. Nos. 4,670,549 and 4,668,776), a benzyl or substituted benzyl group (U.S. Pat. Nos. 4,680,386, and 4,670,549) or a moiety selected from the group consisting of lower alkyl, substituted alkyl, lower alkenyl, aryl substituted methyl, substituted oxalkyl, and substituted thiomethyl groups (U.S. Pat. No. 4,672,109).

6-O-alkyl erythromycin C is a minor fermentation product of the microbial transformation of 6-O-alkyl erythromycin A by *Mucor circinelloides* (McAlpine et al., 27th International Conference of Antimicrobial Agents and Chemotherapy, New York, October 1987). While there are no known methods for the chemical synthesis of 6-O-alkyl erythromycin C, it is theoretically possible to use methods comparable to those described for producing 6-O-alkyl erythromycin A in the preparation of 6-O-alkyl erythromycin C.

As discussed above, erythronolide B, a derivative of erythromycin B, is a known bioprecursor of erythromycins A through D (U.S. Pat. No. 5,141,926). However, 6-O-alkyl derivatives of erythronolide B are not known in the art.

An object of the present invention is to provide novel 6-O-alkyl derivatives of erythronolide B and methods for their preparation. A further object of the present invention is to provide a novel method of preparing 6-O-alkyl erythromycin C using 6-O-alkyl derivatives of erythronolide B as starting materials.

BRIEF SUMMARY OF THE INVENTION

The present invention provides 6-O-alkyl derivatives of erythronolide B and an efficient and practical method of preparing 6-O-alkyl derivatives of erythronolide B.

The preparation of 6-O-alkyl derivatives of erythronolide B starts with acetylating erythromycin B at the 2'-oxygen to form 2'-acetyl erythromycin B. This reaction involves the use of an acetylating agent such as acetic anhydride. 2'-acetyl erythromycin B is alkylated at the 6-position oxygen with an alkylating agent and a base to form 2'-acetyl-6-O-alkyl erythromycin B. Alkylating agents are preferably alkyl halides and the base is preferably potassium hydroxide. The acetyl group is removed from 2'-acetyl-6-O-alkyl erythromycin B by way of hydrolysis with an alcohol and a base to form 6-O-alkyl erythromycin B. The base used in the hydrolysis step is preferably potassium hydroxide or potassium carbonate. 6-O-alkyl erythromycin B is oximated with hydroxylamine and an alcohol at the 9-position to form 6-O-alkyl-9-oxime erythromycin B. The two sugar moieties (i.e., desosamine and cladinose) of 6-O-alkyl-9-oxime erythromycin B are removed by reacting with a hydrogen halide and pyridine to produce 6-O-alkyl-9-oxime erythronolide B. The final step is to deoximate 6-O-alkyl-9-oxime erythronolide B with sodium bisulfite and alcohol/water to form 6-O-alkyl erythronolide B. The alcohol used in the deoximation step is preferably ethanol or methanol.

The present invention further provides a novel method for preparing 6-O-alkyl erythromycins A and C when the starting compound is a 6-O-alkyl derivative of erythronolide B.

DETAILED DESCRIPTION OF THE INVENTION

I. Definitions

A number of defined terms are used herein to designate particular elements of the present invention. When so used, the following meanings are intended:

The term "alkyl" refers to saturated, straight or branched-chain hydrocarbon radicals containing between one and ten carbon atoms including, but not limited to, methyl, ethyl, propyl, isopropyl, n-butyl, tert-butyl and neopentyl. More preferably, the alkyl is limited to 1–6 carbons. Most preferably, the alkyl is a methyl group.

The term "alkylating agent" refers to a reagent capable of placing an alkyl group onto a nucleophilic site, including, but not limited to, alkyl halides such as methyl bromide, ethyl bromide, n-propyl bromide, methyl iodide, ethyl iodide, and n-propyl bromide; dialkyl sulfates such as dimethyl sulfate, diethyl sulfate, and di-n-propyl sulfate; and alkyl or aryl sulfonates such as methyl-p-toluenesulfonate, ethyl methanesulfonate, n-propyl methanesulfonate, and the like.

The term "aryl (lower alkyl)" refers to a lower alkyl radical having appended thereto 1–3 aromatic hydrocarbon groups, as for example benzyl, diphenylbenzyl, trityl and phenylethyl.

The term "aryloxy" refers to an aromatic hydrocarbon radical that is joined to the rest of the molecule via an ether linkage (i.e., through an oxygen atom), as for example phenoxy.

The term "cycloalkyl" refers to a saturated monocyclic hydrocarbon radical having from three to eight carbon atoms in the ring and optionally substituted with between one and three additional radicals selected from among lower alkyl, halo (lower alkyl), lower alkoxy, and halogen. Examples of cycloalkyl radicals include, but are not limited to, cyclopropyl, cyclobutyl, cyclopentyl, cyclohexyl, cycloheptyl, 1-fluoro-cyclopropyl, and 2-fluorocyclopropyl.

The term "lower alkenyl" refers to a straight or branched-chain hydrocarbon radical containing between two and six carbon atoms and possessing at least one carbon-carbon double bond. Examples of lower alkenyl radicals include vinyl, allyl, 2- or 3-butenyl, 2-, 3- or 4-pentenyl, 2-, 3-, 4- or 5-hexenyl and isomeric forms thereof.

The term "lower alkoxy" refers to a lower alkyl radical that is joined to the rest of the molecule via an ether linkage (i.e., through an oxygen atom). Examples of lower alkoxy radicals include, but are not limited to, methoxy and ethoxy.

The term "lower alkyl" refers to an alkyl radical containing one to six carbon atoms including, but not limited to, methyl, ethyl, propyl, isopropyl, n-butyl, tert-butyl and neopentyl.

The term "polar aprotic solvent" refers to polar organic solvents lacking an easily removable proton, including, but not limited to, N,N-dimethylformamide, dimethyl sulfoxide, N-methyl-2-pyrrolidone, hexamethylphosphoric triamide, tetrahydrofuran, 1,2-dimethoxyethane, acetonitrile or ethyl acetate, and the like.

The term "strong alkali metal base" refers to an alkali metal base having a weak conjugate acid, including, but not limited to, sodium hydroxide, potassium hydroxide, sodium hydride, potassium hydride, potassium t-butoxide, and the like.

The term "substituted aryl (lower alkyl)" refers to an aryl (lower alkyl) residue as defined above having between one and three non-hydrogen ring substituents, each independently selected from among halogen, lower alkoxy, lower alkyl, hydroxy-substituted lower alkyl, and (lower alkyl) amino. Examples of substituted aryl (lower alkyl) radicals include 2-fluorophenylmethyl, 4-fluorophenylethyl and 2,4-difluorophenylpropyl.

The term "weak organic amine base" refers to an organic amine base having a strong conjugate acid, including, but not limited to trimethylamine, triethylamine, tripropylamine, pyridine, 2-methoxypyridine, 1-methylpyrrolidine, 1-methylpiperidine, and 1-ethylpiperidine, and the like.

II. Compound

In one aspect, the present invention provides a novel compound (Compound I) that is a 6-O-alkyl derivative of erythromycin B and has the general formula:

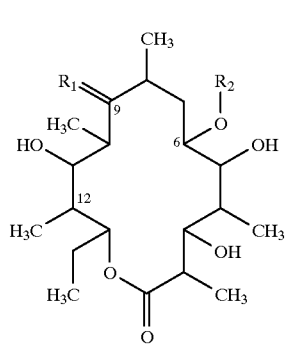

I where $R^1$ is oxygen or NOH, and $R^2$ is hydrogen or alkyl.

Compound I is shown without spatial bond orientation and, thus, defines all combinations of bond orientation and is intended to cover all possible stereo-configurations (e.g., epimers). For the same reason, the diagrams shown below are also drawn without spatial bond orientations. In a preferred embodiment, however, the spatial bond orientations of Compound I are the same as shown above for Clarithromycin A and B.

III. Process of Making a 6-O-Alkyl Derivative of Erythronolide B

Another aspect of the present invention is a method for preparing a 6-O-alkyl derivative of erythromycin B. Generally, the process includes protecting the 2'-hydroxyl group before alkylating at the C-6 position, and then deprotecting the 2'-hydroxyl group. Protection of the 9-oxygen then takes place before the sugar groups are removed. Thereafter, the 9-oxygen is deprotected to provide a 6-O-alkyl derivative of erythronolide B.

A process of the present invention begins with erythromycin B (Compound II), typically produced using fermentation. As shown below, the 2'-hydroxyl group of Compound II is first O-protected to form Compound III before alkylation can take place. This O-protection step can be accomplished using conventional O- or N-protecting groups.

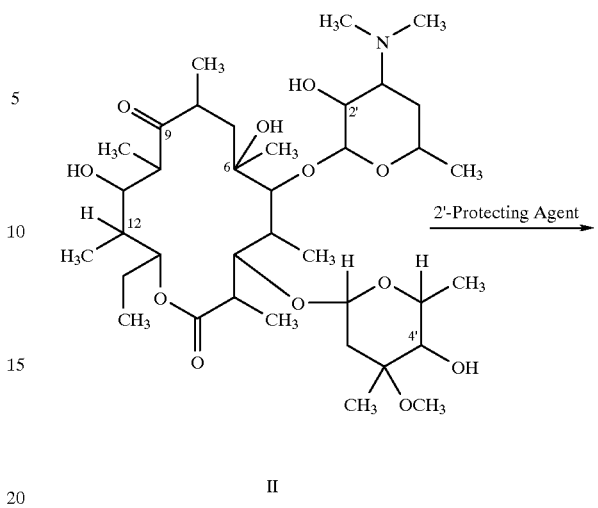

II

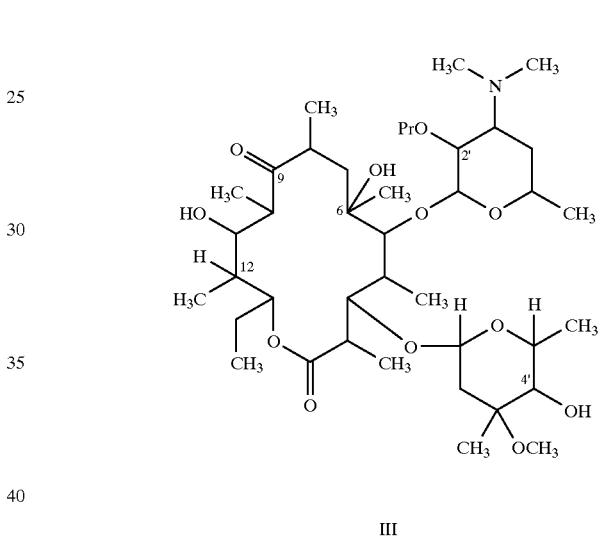

III

Exemplary and preferred O-protecting groups are alkoxycarbonyls (e.g., methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, methyloxycarbonyl and the like), alkoxyalkoxycarbonyls (e.g., methoxymethoxycarbonyl, ethoxymethoxy-carbonyl, 2-methoxyethoxycarbonyl, 2-ethoxyethoxycarbonyl, 2-butoxyethoxy-carbonyl, 2-methoxyethoxymethoxycarbonyl and the like), haloalkoxycarbonyls (e.g., 2-chloroethoxycarbonyl, 2-chloroethoxycarbonyl, 2,2,2-trichloroethoxy-carbonyl and the like), unsaturated alkoxycarbonyls (e.g., allyloxycarbonyl, pro-pargyloxycarbonyl, 2-butenoxycarbonyl, 3-methyl 2-butenoxycarbonyl and the like), substituted benzyloxycarbonyls (e.g., benzyloxycarbonyl, p-methylbenzyloxycarbonyl, p-methoxybenzyloxycarbonyl, p-nitro-benzyloxycarbonyl, 2,4-dinitrobenzyloxycarbonyl, 3,5-di-methylbenzyl-oxycarbonyl, p-chlorobenzyloxy-carbonyl, p-bromobenzyloxycarbonyl and the like) and substituted phenoxycarbonyls [e.g., phenoxycarbonyl, p-nitrophenoxycarbonyl, o-nitrophenoxy-carbonyl, 2,4-di-nitrophenoxycarbonyl, p-methylphenoxycarbonyl, m-methyl-phenoxycarbonyl, o-bromophenoxycarbonyl, 3,5-dimethylphenoxycarbonyl, p-chlorophenoxycarbonyl, 2-chloro 4-nitro-phenoxycarbonyl and the like (See, e.g., Greene and Wuts' *Protective Groups in Organic Synthesis*, 2d. Ed. John Wiley & Sons, Inc., New York, 1991, the disclosure of which is incorporated herein by reference).

Exemplary and preferred lower alkyl monocarbonyl groups are acetyl, propionyl, butyryl, isobutyryl and the like. Exemplary and preferred lower alkenyl monocarbonyl groups include acryloxyl, methacryloxy and the like. Exemplary and preferred lower alkoxycarbonyl-alkylcarbonyl groups include methoxy-carbonyl-methylcarbonyl, ethoxycarbonyl-methylcarbonyl, ethoxycarbonyl-ethylcarbonyl and the like. Exemplary and preferred arylcarbonyl groups include benzoyl, p-methoxybenzoyl, 3,4,5-trimethoxybenzoyl, p-chlorobenzoyl, 2,4-dichlorobenzoyl, 3,5-dichlorobenzoyl, diphenylacetyl, 1-naphthaleneacetyl, 2-naphthaleneacetyl and the like. Exemplary and preferred silyl groups have the formula:

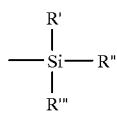

where R', R", and R'" are independently hydrogen, lower alkyl, aryl, phenyl, phenyl substituted lower alkyl, cycloalkyl or alkenyl.

The use of O-protecting groups in the preparation of erythromycin derivatives has been described (See, e.g., U.S. Pat. No. 4,672,109, and European Patent Application 0260938A2, the disclosures of which are incorporated herein by reference).

Conventional O-protecting groups, as set forth above, are positioned using standard procedures well known in the art. In the most preferred embodiment, an acetyl group can be positioned at the 2'-position by reacting Compound II with an acetylating agent and a base. Suitable acetylating agents that can be used include anhydride and acid halide compounds of the formula $(R^5CO)_2O$ or $R^5COCl$, where $R^5$ is hydrogen or a substituent group such as lower alkyl (e.g., methyl, ethyl, n-propyl, isopropyl, n-butyl, sec-butyl, t-butyl and the like) or aryl (e.g., phenyl, p-methoxyphenyl, p-chlorophenyl, m-chlorophenyl, o-chlorophenyl, 2,4,-dichlorophenyl, p-bromophenyl, m-nitrophenyl, p-nitrophenyl, benzhydryl, 1-naphthyl and the like). Suitable bases are organic bases such as triethylamine, pyridine and diethylamine. A most preferred base is ethyl acetate.

One of skill in the art will readily appreciate that it may be advantageous to also substitute for a methyl group of the dimethylamino moiety at the 3'-position of erythromycin A using a conventional N-protecting group. Exemplary and preferred N-protecting groups are alkoxycarbonyl groups (e.g., a methoxy-carbonyl group, an ethoxycarbonyl group, an isopropoxycarbonyl group, an n-propoxycarbonyl group, an n-butoxycarbonyl group, an isobutyloxycarbonyl group, a sec-butyloxycarbonyl group, a t-butyloxycarbonyl group, a 2-ethyl-hexyloxycarbonyl group, a cyclohexyloxycarbonyl group, a methyloxy-carbonyl group and the like); alkoxyalkoxycarbonyl groups (e.g., a methoxymethoxycarbonyl group, an ethoxymethoxycarbonyl group, a 2-methoxyethoxycarbonyl group, a 2-ethoxyethylcarbonyl group, a 2-ethoxyethoxycarbonyl group, a 2-butoxyethoxycarbonyl group, a 2-methoxyethoxymethoxycarbonyl group and the like); haloalkoxycarbonyl groups (e.g., a 2-chloroethoxycarbonyl group, a 2-chloroethoxycarbonyl group, a 2,2,2-trichloroethoxycarbonyl group and the like), unsaturated alkoxycarbonyl groups (e.g., an allyloxycarbonyl group, a propargyloxycarbonyl group, a 2-butenoxycarbonyl group, a 3-methyl-2-buten-oxycarbonyl group and the like), substituted benzyloxycarbonyl groups (e.g., a benzyloxycarbonyl group, a p-methylbenzyloxycarbonyl group, a p-methoxybenzyloxycarbonyl group, a p-nitrobenzyloxycarbonyl group, a 2,4-dinitrobenzyl-oxycarbonyl group, a 3,5-dimethylbenzyloxycarbonyl group, a p-chlorobenzyl-oxycarbonyl group, a p-bromobenzyloxycarbonyl group and the like), and substituted phenoxycarbonyl groups [e.g., a phenoxycarbonyl group, a p-nitrophenoxycarbonyl group, an o-nitrophenoxycarbonyl group, a 2,4-dinitro-phenoxycarbonyl group, a p-methylphenoxycarbonyl group, an m-methyl-phenoxycarbonyl group, an o-bromophenoxycarbonyl group, a 3,5-dimethyl-phenoxycarbonyl group, a p-chloro-phenoxycarbonyl group, a 2-chloro-4-nitro-phenoxycarbonyl group and the like (U.S. Pat. No. 4,672,109)].

The dimethylamino moiety at the 3'-position may also be protected as a quaternary salt by reacting with a 3'-dimethylamino derivative A-X, wherein A is a 2-alkenyl group, a benzyl group or a substituted benzyl group; and X is a halogen atom (See, e.g., U.S. Pat. No. 4,670,549).

Following protection, Compound III is selectively alkylated to produce Compound IV. Procedures and reagents for alkylating the 6-position of Compound III are well known in the art (See, e.g., U.S. Pat. Nos. 4,672,109 and 4,670,549). This alkylation step is depicted as follows:

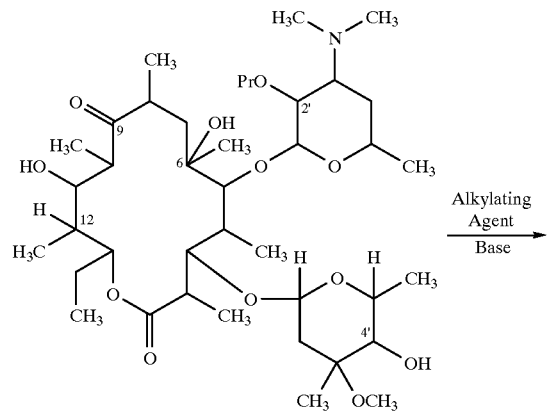

III

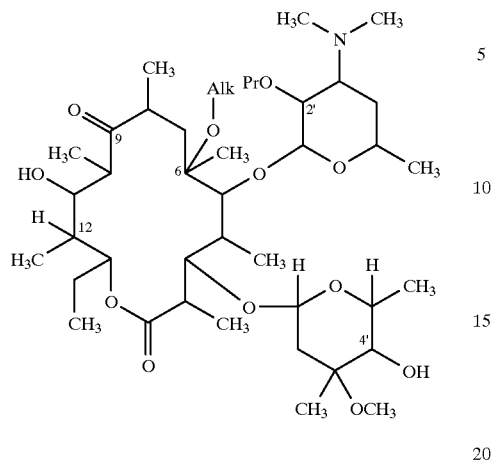

IV

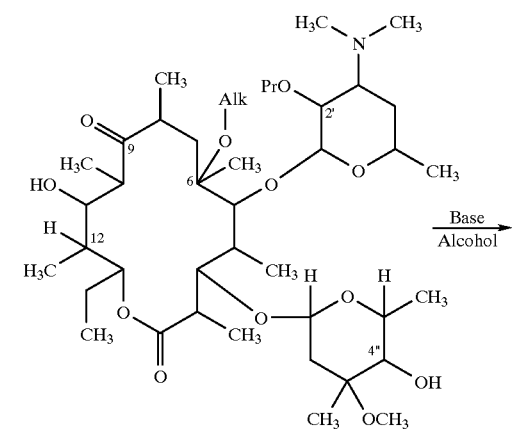

IV $\xrightarrow{\text{Base}}{\text{Alcohol}}$

Briefly, the hydroxyl-protected compound is reacted with a suitable alkylating agent in the presence of a base. Exemplary and preferred alkylating agents are alkyl halides such as methyl bromide, ethyl bromide, n-propyl bromide, methyl iodide, ethyl iodide, n-propyl bromide, dimethyl sulfate, diethyl sulfate, di-n-propyl sulfate, methyl-p-toluenesulfonate, ethyl methanesulfonate, and n-propyl methanesulfonate.

Exemplary and preferred bases are a strong alkali metal base, preferably selected from the group consisting of an alkali metal hydride, alkali metal hydroxide or alkali metal alkoxide, and a weak organic amine base, preferably selected from the group consisting of trimethylamine, triethylamine, tripropyl-amine, pyridine, 2-methoxypyridine, 1-methylpyrrolidine, 1-methylpiperidine, and 1-ethylpiperidine.

The alkylation step is carried out in a suitable solvent that includes methyl-t-butyl ether. Exemplary and preferred solvents are polar aprotic solvents such as N, N-dimethylformamide, dimethyl sulfoxide, N-methyl-2-pyrrolidone, hexamethylphosphoric triamide, tetrahydrofuran, 1,2-dimethoxyethane, acetonitrile or ethyl acetate, or a mixture of such polar aprotic solvents maintained at a reaction temperature and for a period of time sufficient to effect alkylation, preferably from −15° C. to room temperature for a period of 1 to 8 hours.

The protecting groups are removed from Compound IV using methods known in the art to form Compound V (shown below).

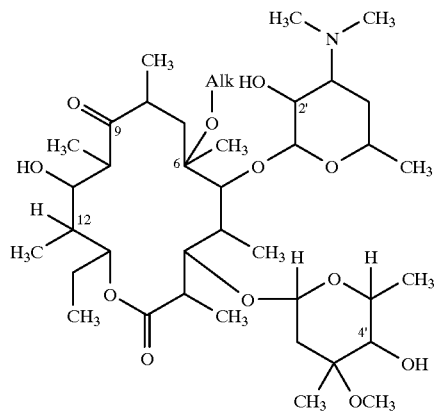

V

A preferred method for removing the protecting group on the 2'-carbon position is to hydrolyze Compound IV with a base and alcohol. The base used is preferably potassium carbonate.

Compound V is next protected at the 9-oxygen position using standard procedures well known in the art to produce Compound VI, as shown below.

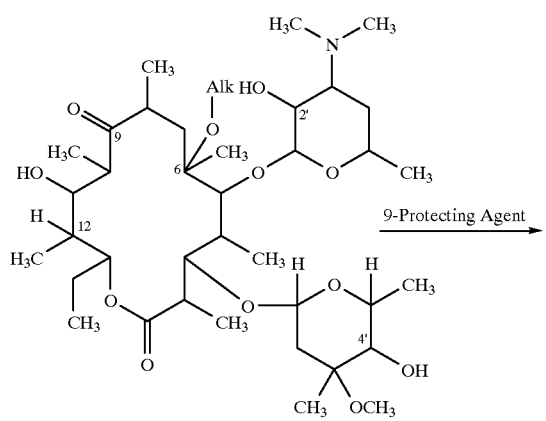

V

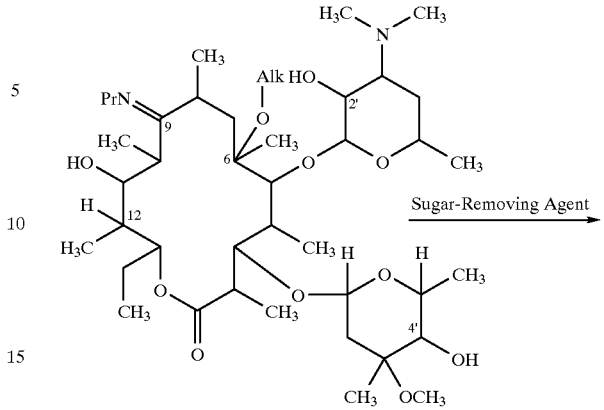

VI

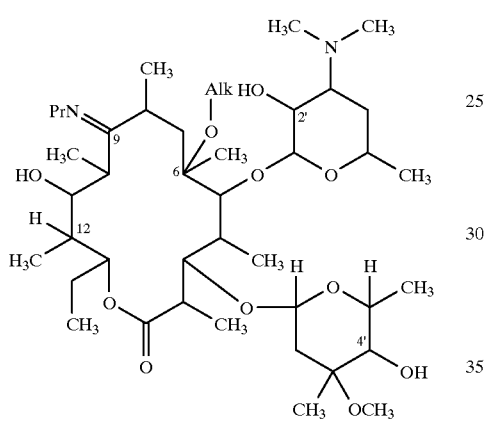

VI

By way of example, Compound V is oximated with either hydroxylamine hydrochloride and a base, free hydroxylamine in methanol, or hydroxylamine and an organic acid (See, e.g., U.S. Pat. No. 5,274,085, the disclosure of which is incorporated herein by reference). Preferably, this protection step is accomplished using hydroxylamine and formic acid.

After protection at the 9-oxygen position, the sugar moieties (i.e., desosamine and cladinose) of Compound VI are removed using methods known in the art to produce Compound I-C (shown below).

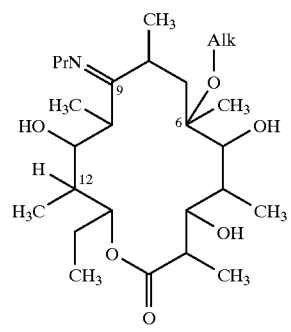

I-C

An exemplary means for removing the sugar moieties is through glycoside removal. Briefly, this is accomplished by reacting Compound VI with hydrogen halide in a solvent and quenching in a base. The resulting filtrate is extracted with a solvent and dried with a base. The solvent is then filtered and distilled, and removed by a chase reaction. Compound VI is collected via filtration after refrigeration overnight.

Lastly, Compound I-C is deprotected utilizing methods known in the art to form Compound I-A (shown below).

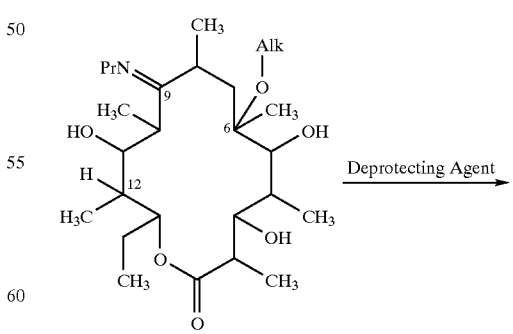

I-C

-continued

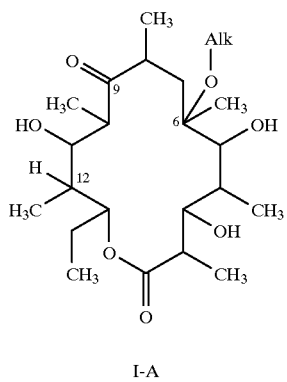

I-A

In a preferred embodiment, when protection at the 9-carbon position is accomplished through oximation, removal of the protecting group takes place by way of deoximation. Deoximation is carried out in accordance with standard procedures known in the art (See e.g., U.S. Pat. No. 4,672,109). Briefly, Compound I-C is reacted with sodium hydrogen sulfite in alcohol (e.g., ethanol) and refluxed. The solution is cooled, alkalinized and precipitated with aqueous alkali metal bicarbonate. The precipitate formed in the above reaction is collected by filtration, washed and recrystallized with alcohol to provide Compound I-A.

The complete process for preparing novel 6-O-alkyl derivatives of erythronolide B is shown in Scheme 1 below. Specifically, Scheme 1 shows the preferred embodiment of the present invention in that the alkylating agent used is methyl bromide. As such, Scheme 1 depicts the preparation of 6-O-methyl derivatives of erythronolide B. The end product of Scheme 1 is novel Compound I-B.

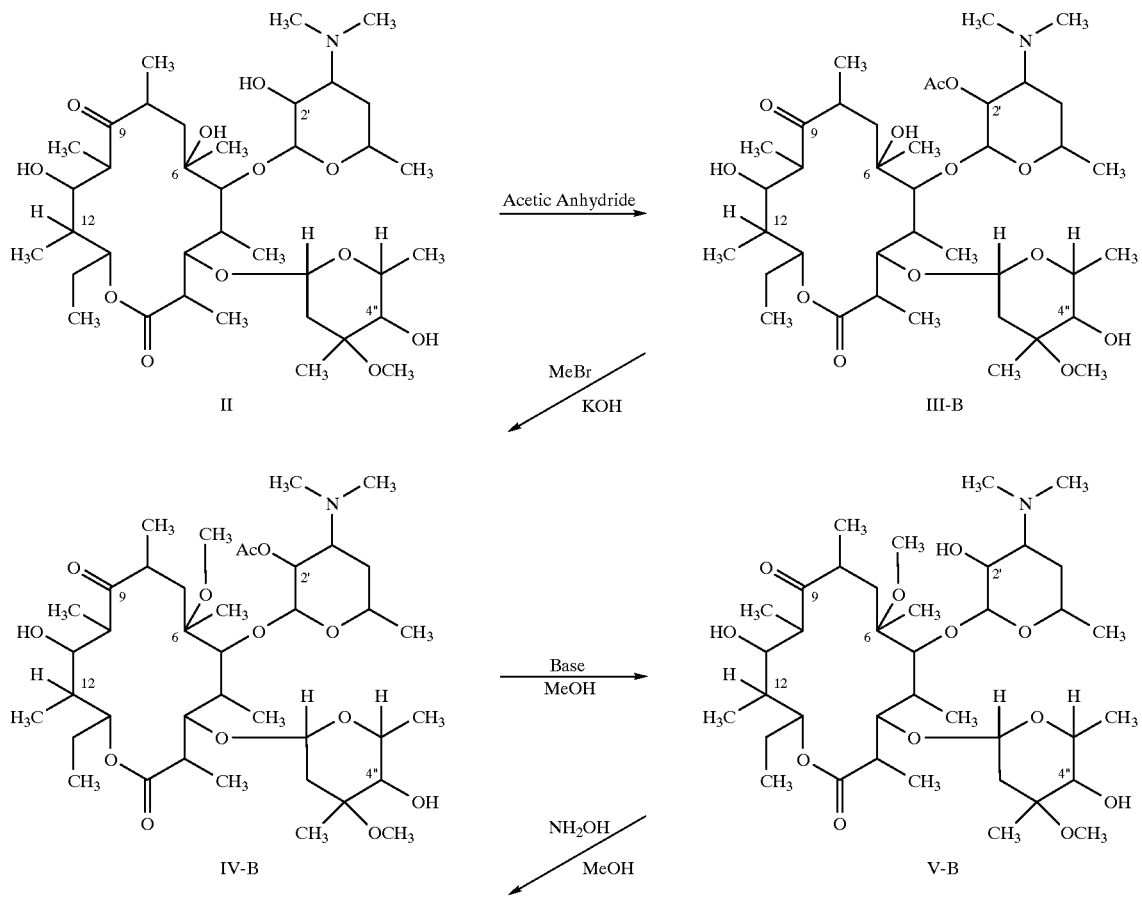

Scheme 1

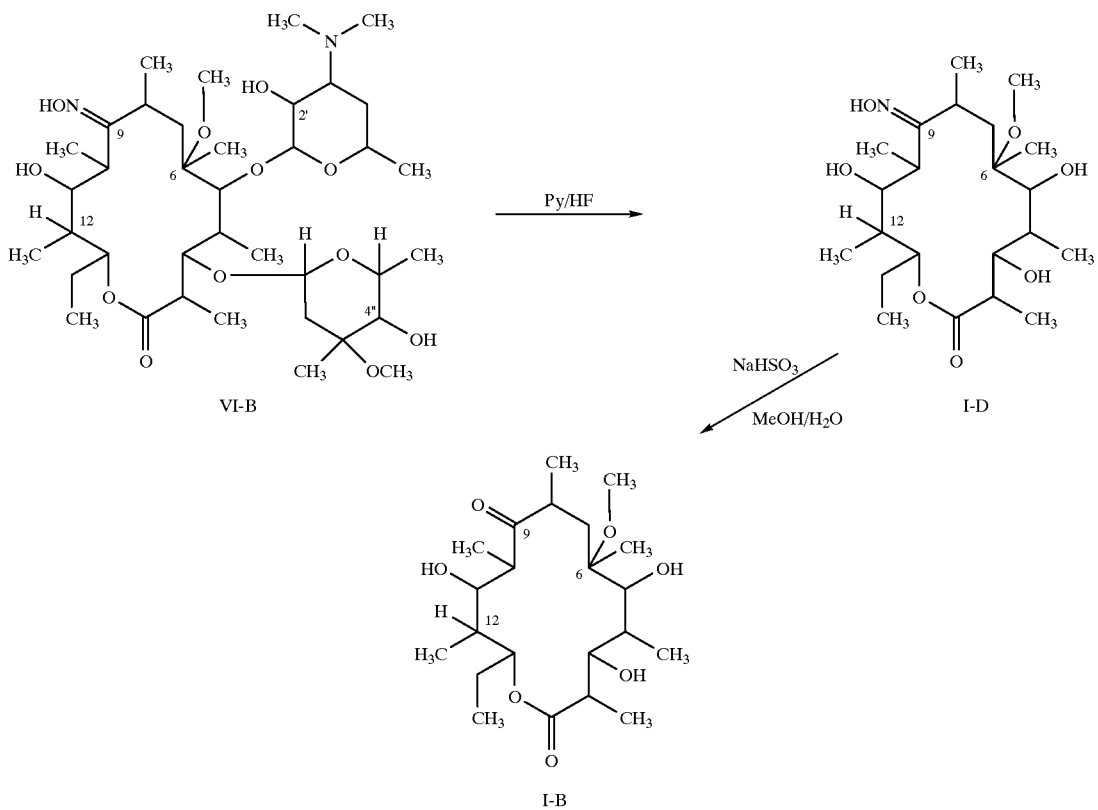

IV. Process of Making Clarithromycins A and C

The present invention further provides a novel method for preparing 6-O-alkyl erythromycins A and C. This method is similar to the process disclosed in U.S. Pat. No. 5,141,926. However, that patent does not disclose using a 6-O-alkylated derivative of erythronolide B. Scheme 2 below displays the novel process of the present invention for the preparation of 6-O-alkyl erythromycins A and C.

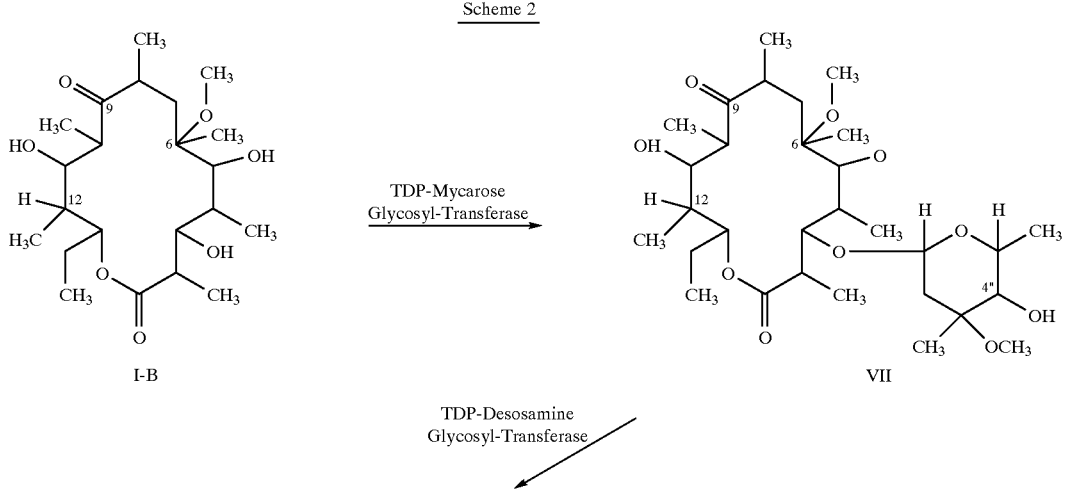

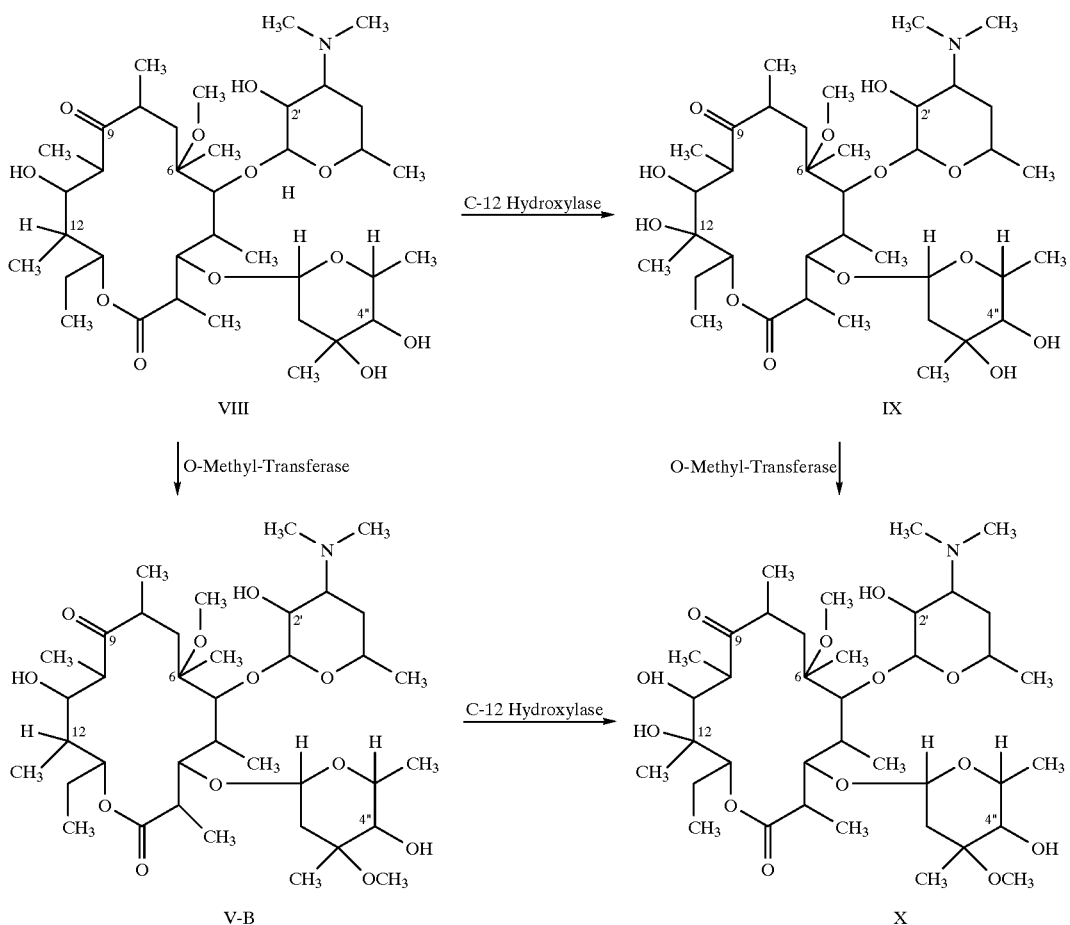

The process of Scheme 2 begins with the enzymatic addition of a sugar moiety at the 3-carbon position of Compound I-B (6-O-methyl erythronolide B), resulting in the formation of intermediate Compound VII (3-"-6-O-methyl-mycarosyl erythronolide B). Another sugar moiety is enzymatically added at the 5-carbon position of Compound VII to produce Compound VIII (6-O-methyl erythromycin D, 6-O-alkyl erythromycin D). At this point, two possible processes may be undertaken to produce Compound X (6-O-methyl erythromycin A, 6-O-alkyl erythromycin A). Under the first path, hydroxylation at the 12-carbon position of Compound VIII replaces hydrogen with a hydroxyl group to produce Compound IX (6-O-methyl erythromycin C, 6-O-alkyl erythromycin C). Then, Compound X is prepared by enzymatically replacing the hydroxyl group at 3"-position of Compound IX with an O-methyl group. By way of the second path, enzymatic O-methyl addition at the 3"-position occurs first, resulting in the formation of Compound V-B (6-O-methyl erythromycin B. 6-O-alkyl erythromycin B). A hydroxyl group replaces the 12-position hydrogen of Compound V via a hydroxylation reaction to produce Compound X. Thus Scheme 2 shows novel methods of preparing 6-O-alkyl erythromycins A through D through the use of novel Compound I-B as the starting material. Specifically, 6-O-alkyl erythromycins A and C may now be produced in a more efficient manner using the novel method of the present invention.

The following Examples illustrate preferred embodiments of the present invention and are not limiting on the specification and claims in any way.

Example 1: Preparation of 2'-Acetyl Erythromycin B

Into a 1.0 L one neck round bottom flask were placed 50 g of erythromycin B (69.64 m mole), 500 mL ethyl acetate and 16 mL acetic anhydride (17.3 g, 169.6 m mole). The solution was stirred at room temperature overnight. Copious amounts of white solids were observed. This mixture was filtered to give 26.2 g solid. The filtrate was washed with 300 mL 5% sodium bicarbonate twice, and the organic layer was dried with magnesium sulfate. The solvent was removed by vacuum distillation to give a second crop of desired product (22.3 g). The product was identified by mass spectroscopy and NMR.

Example 2: Preparation of 2'-Acetyl-6-O-Methyl Erythromycin B

Into a 1.0 L flask equipped with a thermometer, a stirrer, and a drying tube, were placed 137 mL tetrahydrofuran, 137 mL dimethyl sulfoxide and 23 g of 2'-acetyl erythromycin B (30.3 m mole). The solution was cooled with an ice bath to 0–5° C. and followed by addition of 6.2 g triethylamine, 7 mL of methyl bromide (12.11 g, 127.5 m mole) and 3.0 g powdered KOH (45.5 m mole). The temperature of the solution rose temporarily to 6° C. but returned to the cooling bath temperature soon thereafter. After 44 minutes the reaction quenched with 550 mL heptane and 110 mL 2N sodium hydroxide. The layers were separated and the organic phase was washed with 220 mL water, whereupon some solids appeared. The solids were filtered, 9.6 g and the filtrate concentrated to one-third volume under vacuum. More solids appeared and were filtered, 6.6 g; total amount: 16.2 g. The structure was confirmed by proton and C-13 NMR and mass spectroscopy.

Example 3: Preparation of 6-O-Methyl Erythromycin B

To 600 mL methanol and 300 mL alcohol, were added 8.4 g of 2'-acetyl-6-O-methyl erythromycin B (10.9 m mole). The solution and 300 mL of 5% potassium carbonate were stirred for three days. The volume of the resulting solution was reduced to 200 mL under vaccum. Solids were filtered and dried to give 7.37 g of the product.

Example 4: 6-O-Methyl-9-Oxime Erythromycin B

A 1.0 L three-necked flask was first equipped with a thermometer, a condenser, and a stirrer. Then, 7.1 g of 6-O-methyl erythromycin B (9.7 m mole), 300 mL of methanol, 93 g of hydroxylamine (50% solution) and 32 g of formic acid (85%) were added to the flask. The solution was heated to 65° C. for three hours and then further heated to 69–72° C. for sixteen hours. Another 12 g of hydroxylamine and 5 g of formic acid were added and heated at the same temperature for another sixteen hours. The heating mantle was removed and replaced with an ice bath. Under this cooling bath, 250 mL of 2N sodium hydroxide was added to alkalinize the solution, whereupon solids appeared. The solids were collected by filtration and 4.84 g of the product was obtained.

Example 5: Preparation of 6-O-Methyl-9-Oxime Erythronolide B 4.0 g (5.4 m mole) of 6-O-methyl-9-oxime erythromycin B were slowly added to 80 mL of hydrogen fluoride in pyridine (70% HF, 30% pyridine) at room temperature in a Teflon flask. The dark brown solution was stirred at this temperature for 48 minutes and then slowly quenched into 1.6 L of 2 N sodium hydroxide solution. The resulting dark brown solids were removed by filtration and the clear filtrate was extracted twice with 300 mL of methylene chloride. The combined methylene chloride solution was dried with magnesium sulfate, filtered, and the solvent removed by vacuum distillation. The residual pyridine was removed by 60 mL of toluene chase followed by 40 mL of chase under vacuum. The final volume of the toluene solution was 30 mL, and this solution was left in the refrigerator overnight. The crystal was collected by filtration, and 1.16 g (2.7 m mole, 50.2% yield) of the product was obtained.

Example 6: Preparation of 6-O-Methyl Erythronolide B

To dissolve 1.3 g (3 m mole) of 6-O-methyl-9-oxime erythronolide B, the compound was added to 42 mL of 3A alcohol (5% methanol in ethanol), 42 mL water, and then 1.6 g of sodium bisulfite and 0.28 g of formic acid (85%). The mixture was refluxed for one hour and cooled to room temperature. It was observed that crystals slowly appeared. The solid was collected by filtration, and 0.8 g of the product was obtained (64% yield). The structure was identified by proton and C-13 NMR and high resolution mass spectroscopy.

What is claimed is:

1. A compound having the formula:

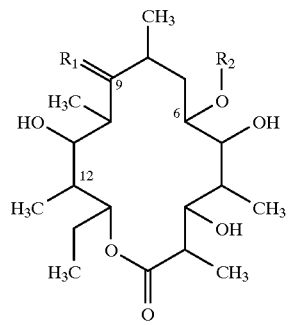

wherein $R^1$ is oxygen or NOH and $R^2$ is alkyl.

2. A process for preparing a 6-O-alkyl derivative of erythronolide B comprising the steps of:

(a) acetylating erythromycin B to form 2'-acetyl erythromycin B;

(b) alkylating the 2'-acetyl erythromycin B to form 2'-acetyl-6-O-alkyl erythromycin B;

(c) removing the acetyl group from the 2'-acetyl-6-O-alkyl erythromycin B to form 6-O-alkyl erythromycin B;

(d) oximating the 6-O-alkyl erythromycin B to form 6-O-alkyl-9-oxime erythromycin B;

(e) removing glycoside from the 6-O-alkyl-9-oxime erythromycin B to form 6-O-alkyl-9-oxime erythronolide B; and (f) deoximating the 6-O-alkyl-9-oxime erythronolide B to provide 6-O-alkyl erythronolide B.

3. The process of claim 2 wherein the erythromycin B is reacted with acetic anhydride.

4. The process of claim 2 wherein the 2'-acetyl erythromycin B is reacted with an alkylating agent and a base.

5. The process of claim 4 wherein the alkylating agent is an alkyl iodide or an alkyl bromide.

6. The process of claim 4 wherein the base is potassium hydroxide.

7. The process of claim 2 wherein the 2'-acetyl 6-O-alkyl erythromycin B is reacted with a methanolic base.

8. The process of claim 7 wherein the base is potassium hydroxide or potassium carbonate.

9. The process of claim 2 wherein the 6-O-alkyl erythromycin B is reacted with hydroxylamine and methanol.

10. The process of claim 2 wherein the 6-O-alkyl-9-oxime erythromycin B is reacted with a hydrogen halide and pyridine.

11. The process of claim 10 wherein the hydrogen halide is hydrogen bromide, hydrogen fluoride, hydrogen chloride, hydrogen iodide, or hydrogen astatine.

12. The process of claim 2 wherein the 6-O-alkyl-9-oxime erythronolide B is reacted with sodium bisulfite and alcohol/water.

13. The process of claim 12 wherein the alcohol is ethanol or methanol.

* * * * *